US009132196B2

(12) United States Patent
De Kort et al.

(10) Patent No.: US 9,132,196 B2
(45) Date of Patent: Sep. 15, 2015

(54) PALATABLE NUTRITIONAL COMPOSITION COMPRISING A NUCLEOTIDE AND/OR A NUCLEOSIDE AND A TASTE MASKING AGENT

(71) Applicant: N.V. Nutricia, Zoetermeer (NL)

(72) Inventors: Esther Jacqueline De Kort, Wageningen (NL); Martine Groenendijk, Barendrecht (NL); Patrick Joseph Gerardus Hendrikus Kamphuis, Utrecht (NL)

(73) Assignee: N. V. Nutricia, Zoetermeer (NL)

( * ) Notice: Subject to any disclaimer, the term of this patent is extended or adjusted under 35 U.S.C. 154(b) by 0 days.

(21) Appl. No.: 14/095,676

(22) Filed: Dec. 3, 2013

(65) Prior Publication Data

US 2014/0162973 A1  Jun. 12, 2014

Related U.S. Application Data

(63) Continuation of application No. 12/809,431, filed as application No. PCT/NL2008/050843 on Dec. 22, 2008, now Pat. No. 8,604,000.

(30) Foreign Application Priority Data

Dec. 20, 2007 (EP) ..................................... 07123811
Mar. 4, 2008 (WO) ................ PCT/NL2008/050124

(51) Int. Cl.
| | | |
|---|---|---|
| *A01N 43/04* | (2006.01) | |
| *A61K 31/70* | (2006.01) | |
| *A61K 47/38* | (2006.01) | |
| *A23L 1/0534* | (2006.01) | |
| *A23L 1/054* | (2006.01) | |
| *A23L 1/29* | (2006.01) | |
| *A23L 1/30* | (2006.01) | |
| *A23L 1/305* | (2006.01) | |
| *A61K 9/00* | (2006.01) | |
| *A61K 31/7052* | (2006.01) | |
| *A61K 31/7072* | (2006.01) | |
| *A61K 33/06* | (2006.01) | |
| *A61K 35/60* | (2006.01) | |
| *A61K 38/02* | (2006.01) | |
| *A61K 47/36* | (2006.01) | |
| *A61K 47/42* | (2006.01) | |
| *A61K 47/44* | (2006.01) | |

(52) U.S. Cl.
CPC ................ *A61K 47/38* (2013.01); *A23L 1/054* (2013.01); *A23L 1/0534* (2013.01); *A23L 1/0545* (2013.01); *A23L 1/296* (2013.01); *A23L 1/305* (2013.01); *A23L 1/3012* (2013.01); *A61K 9/0095* (2013.01); *A61K 31/7052* (2013.01); *A61K 31/7072* (2013.01); *A61K 33/06* (2013.01); *A61K 35/60* (2013.01); *A61K 38/02* (2013.01); *A61K 47/36* (2013.01); *A23V 2002/00* (2013.01); *A61K 47/42* (2013.01); *A61K 47/44* (2013.01)

(58) Field of Classification Search
None
See application file for complete search history.

(56) References Cited

U.S. PATENT DOCUMENTS

| | | |
|---|---|---|
| 3,600,197 A | 8/1971 | Spangler et al. |
| 5,378,488 A | 1/1995 | Dimler et al. |
| 5,886,037 A | 3/1999 | Klor et al. |
| 6,689,467 B1 | 2/2004 | Joubert et al. |
| 6,835,750 B1 | 12/2004 | Henderson |
| 7,090,879 B2 | 8/2006 | Albrecht et al. |
| 8,282,965 B2 | 10/2012 | De Kort et al. |
| 8,283,335 B2 | 10/2012 | Hageman et al. |
| 8,361,989 B2 | 1/2013 | Groenendijk et al. |
| 2003/0114415 A1 | 6/2003 | Wurtman et al. |
| 2004/0001817 A1 | 1/2004 | Giampapa |
| 2005/0208179 A1 | 9/2005 | Albrecht et al. |
| 2006/0025376 A1 | 2/2006 | Wurtman |
| 2006/0241077 A1 | 10/2006 | Wurtman et al. |
| 2007/0004670 A1 | 1/2007 | Wurtman et al. |

(Continued)

FOREIGN PATENT DOCUMENTS

| | | |
|---|---|---|
| EP | 0 175 468 A2 | 3/1986 |
| EP | 0 891 719 A1 | 1/1999 |

(Continued)

OTHER PUBLICATIONS

"Derivative—Definition and More from the Free Merriam-Webster Dictionary" Retrieved Oct. 22, 2012 from http/www.merriam-webster.com/dictionary/derivative.

(Continued)

*Primary Examiner* — Patrick Lewis
(74) *Attorney, Agent, or Firm* — Gilberto M. Villacorta; Sunit Talapatra; Foley & Lardner LLP

(57) ABSTRACT

The present invention relates to the use of a taste masking agent selected from the group of starch; cellulose; xanthan gum; gellan gum; alginate; galactomannans such as fenugreek, guar gum, tara gum, locust bean gum, and cassia gum; gum karaya; gum tragacanth; carrageenan; and mixture thereof, for improving one or more of mouth feel, taste, aftertaste and smell of a liquid aqueous nutritional composition comprising a nucleoside and/or a nucleotide. It also relates to a nutritional composition comprising an unsavoury nucleoside and/or nucleotide component, having improved sensory characteristics such as improved mouth feel, taste, aftertaste and smell. In particular, it relates to a composition comprising said unsavoury nucleoside and/or nucleotide component, in particular comprising an uridine-containing nucleoside and/or a nucleotide in combination with an unsavoury edible oil, such as a fish oil.

15 Claims, 4 Drawing Sheets

(56) References Cited

U.S. PATENT DOCUMENTS

| | | |
|---|---|---|
| 2007/0140992 A1 | 6/2007 | Schick et al. |
| 2010/0323982 A1 | 12/2010 | Hageman et al. |
| 2010/0331258 A1 | 12/2010 | Kamphuis et al. |
| 2010/0331275 A1 | 12/2010 | Groenendijk et al. |
| 2011/0006917 A1 | 1/2011 | Taniguchi et al. |
| 2011/0009357 A1 | 1/2011 | Hageman et al. |
| 2011/0027391 A1 | 2/2011 | De Kort et al. |
| 2011/0105594 A1 | 5/2011 | De Kort et al. |
| 2013/0012469 A1 | 1/2013 | De Kort et al. |
| 2013/0018012 A1 | 1/2013 | Hageman et al. |

FOREIGN PATENT DOCUMENTS

| | | |
|---|---|---|
| EP | 1 216 041 B1 | 2/2004 |
| EP | 1 656 839 A1 | 5/2006 |
| EP | 1 666 092 A2 | 6/2006 |
| EP | 1 800 675 A1 | 6/2007 |
| EP | 1 282 365 B1 | 12/2007 |
| JP | 01-080250 A | 3/1989 |
| JP | 06-237734 A | 8/1994 |
| JP | 10-004918 A | 1/1998 |
| JP | 10-136937 A | 5/1998 |
| JP | 11-071274 A | 3/1999 |
| WO | WO-94/05319 A1 | 3/1994 |
| WO | WO-00/38829 A1 | 7/2000 |
| WO | WO-01/32034 A1 | 5/2001 |
| WO | WO-01/82928 | 11/2001 |
| WO | WO-02/088159 A1 | 11/2002 |
| WO | WO-02/096464 A1 | 12/2002 |
| WO | WO-03/013276 A1 | 2/2003 |
| WO | WO-03/041701 A2 | 5/2003 |
| WO | WO-2005/039597 A2 | 5/2005 |
| WO | WO-2006/031683 A2 | 3/2006 |
| WO | WO-2006/118665 A2 | 11/2006 |
| WO | WO-2006/127620 A1 | 11/2006 |
| WO | WO-2006/127620 A2 | 11/2006 |
| WO | WO-2007/001883 A2 | 1/2007 |
| WO | WO-2007/004685 A2 | 1/2007 |
| WO | WO-2007/004689 A1 | 1/2007 |
| WO | WO-2007/008586 A2 | 1/2007 |
| WO | WO-2007/058538 A2 | 5/2007 |
| WO | WO-2007/073178 A2 | 6/2007 |
| WO | WO-2009/002145 A1 | 12/2008 |
| WO | WO-2009/002146 A1 | 12/2008 |
| WO | WO-2009/002148 A1 | 12/2008 |
| WO | WO-2009/002163 A1 | 12/2008 |
| WO | WO-2009/002164 A1 | 12/2008 |
| WO | WO-2009/002165 A1 | 12/2008 |
| WO | WO-2009/002166 A1 | 12/2008 |
| WO | WO-2009/082203 A1 | 7/2009 |
| WO | WO-2009/082227 A1 | 7/2009 |

OTHER PUBLICATIONS

Albert, M. et al. "Preclinical prediction of AD using neuropsychological tests", Journal of the International Neuropsychological Society, 2001, vol. 7, pp. 631-639.

Bird, T.D., Genetic aspects of Alzheimer disease, Genetics in Medicine, Apr. 2008, vol. 10, No. 4, p. 231-237.

Cansev, M. et al. "Chronic Administration of Docosahexaenoic Acid or Eicosapentaenoic Acid, But Not Arachidonic Acid, Alone or in Combination with Uridine, Increases Brain Phosphatide and Synaptic Protein Levels in Gerbils", Neuroscience, 2007, vol. 148, pp. 421-431.

Cansev, M. et al. "Oral administration of circulating precursors for membrane phosphatides can promote the synthesis of new brain synapses", Alzheimer's & Dementia, 2008, vol. 4, pp. S153-S168.

Cole, G. et al. "Docosahexaenoic Acid Protects From Amyloid and Dendritic Pathology in an Alzheimer's Disease Mouse Model", Nutrition and Health, 2006, vol. 18, pp. 249-259.

Database WPI Week 198918, Derwent Publications Ltd., London, GB, AN 1989-134762, JP 01 080250, Mar. 27, 1989 [XP002449815].

Database WPI Week 199182, Derwent Publications Ltd., London, GB, AN 1998-123754, JP 10 004918, Jan. 13, 1998 [XP002470089], 1 page.

Database WPI Week 199439, Thomson Scientific, London, GB, AN 1994-312783, JP 06 237734, Aug. 30, 1994 [XP002494932], 2 pages.

Database WPI Week 199831, Derwent Publications Ltd., London, GB, AN 1998-355002, JP 10 136937, May 26, 1998 [XP002449814].

Database WPI Week 199921, Thomson Scientific, London, GB, 1999-248435, JP 11 071274, Mar. 16, 1999 [XP002495741].

Diagnostic and Statistical Manual of Mental Disorders (fourth Edition, 2000) 013 DSM-IV-TR; American Psychiatric Association. (table of contents only).

Folstein et al., "'Mini-Mental State' A Practical Method for Grading the Cognitive State of Patients for the Clinician," J Psychiat Res, 1975, 12(3), pp. 189-198.

Freund-Levi, Y. et al. "w-3 Fatty Acid Treatment in 174 Patients with Mild to Moderate Alzheimer Disease: OmegAD Study", Arch Neurol, Oct. 2006, vol. 63, pp. 1402-1408.

Galasko et al., "An Inventory to Assess Activities of Daily Living for Clinical Trials in Alzheimer's Disease," Alz Dis Assoc Dis, 1997, 11(Sup 2), pp. 33-39.

Hansson et al., "Association Between CSF Biomarkers and Incipient Alzheimer's Congnitive Impairment: A Follow-up Study," Lancet Neurol, vol. 5, No. 3, 2006, pp. 228-234.

Holguin, S. et al. "Chronic adminstration of DHA and UMP the impaired memory of environmentally impoverished rats", Behavioural Brain Research, 29, 2008, vol. 191, pp. 11-16.

International Search Report for PCT/NL2008/050124, mailed Dec. 29, 2008.

International Search Report, PCT/NL2008/050843, dated Mar. 17, 2009, 3 pages.

Korezyn, A. et al. "The prevention of the dementia epidemic", Journal of the Neurological Sciences, 2007, vol. 257, pp. 2-4.

Markesbery, W. et al. "Neuropathologic Substrate of Mild Cognitive Impairment", Arch Neurol, Jan. 2006, vol. 63, pp. 38-46.

McKahnn et al., "Clinical diagnosis of Alzheimer's disease: Report of the NINCDS-ADRDA Work Group," Neurology, 1984, 34, pp. 939-944.

Morris, J. "Mild Cognitive Impairment Is Early-Stage Alzheimer Disease", Arch Neurol., 2006, vol. 63, No. 1, 6 pgs.

Nitsch, R. et al. "Evidence for a membrane defect Alzheimer disease braine", Proc. Natl. Acad. Sci., Mar. 1992, vol. 89, pp. 1671-1675.

Oksman, M. "Impact of different saturated fatty acid, polyunsaturated fatty acid and cholesterol containing diets on beta-amyloid accumulation in APP/PSI transgenic mice", Neurobiology of Disease, 2006, vol. 23, pp. 563-572.

Pratico et al., "Increase of Brain Oxidative Stress in Mild Cognitive Impairment," Arch Neurol, vol. 59, 2002, pp. 972-976.

Quadri et al. "Homocysteine, folate, and vitamin B-12 in mild cognitive impairment, Alzheimer disease, and vascular dementia", Am. J. Clin. Nutr., 2004, vol. 80, pp. 114-122.

Reynolds, E. "Vitamin B12, folic acid, and the nervous system", Review, Nov. 2006, vol. 5, pp. 949-960.

Sakamoto, T. et al. "Oral supplementation with docosahexaenoic acid and uridine-5'-monophosphate increases dendritic spine density in adult gerbil hippocampus", Brain Research, 2007, vol. 1182, pp. 50-59.

Wood-Kaczczmar et al. Understanding the molecular causes of Parkinson's disease, Trends in Molecular Medicine, vol. 12, No. 11 (2006), pp. 521-528.

Wurtman et al., "Synaptic Proteins and Phospholipids are Increased in Gerbil Brain by Administering Uridine Plus Docosahexaenoic Acid Orally," Brain Research, 2006, 1088(1), pp. 83-92.

Cormier, et al. "Diet and Child Behavior Prolems: Fact or Fiction?", Pediatric Nursing, Mar.-Apr. 2007, vol. 33, No. 2, pp. 138-143.

Freemantle, et al. "Omega-3 fatty acids, energy substrates, and brain function during aging", Prostaglandins Leukotrienes and Essential Fatty Acids, 2006, vol. 75, pp. 213-220.

Katoku et al., "Nutrient Compositions Containing Nucleic Acid Related Compounds, used for Growth and Health Maintenance—Contain e.g. Docosahexaenoic Acid, Arachidonic Acid and Cholesterol" WPI/THOMSON, Jan. 13, 1998, 1 page [XP002470089].

(56) References Cited

OTHER PUBLICATIONS

Purina Garden Recipe, http://purinasmallanimals.com/SmallAnimals/Gerbil/PurinaGardenRecipeGerbiland . . . , retrieved Oct. 15, 2013, 4 pgs.

Borucki, Hans (Bearb.): schuler Duden der Chemie, 2. Auflage, Mannheim, 1988, pp. 416-419.

Cansev, et al. "Chronic administration of docosahexaenoic acid or eicosapentaenoic acid, but not arachidonic acid, alone or in combination with uridine, increases brain phosphatide and synaptic protein levels in gerbils", Neuroscience, Aug. 24, 2007, vol. 148, No. 2, pp. 421-431.

Cansev, et al. "Oral administration of circulating precursors for membrane phosphatides can promote the synthesis of new brain synapses", Alzheimer's & Dementia, 2008, vol. 4, pp. S153-S168.

Cooper, et al. "The Clinical Assessment of the Patient with Early Dementia", J Neurol Neurosurg Psychiatry, 2005, vol. 76 (Suppl V.), v15-v24.

Folstein, et al. "A Practical Method for Grading the Cognitive State of Patients for the Clinician", J. Psychiat. Res., 1975, vol. 12, pp. 189-198.

Garcia, et al. "Daily larval growth and RNA and DNA content of the NW Mediterranean anchovy *Engraulis encrasicolus* and their relations to the environment", Marine Ecology Progress Series, May 28, 1998, vol. 166, pp. 237-245.

Gluck, et al. "Psychobiolgical Models of Hippocampal Function in Learning and Memory", Neurobilogy of Learning and Memory, Academic Press, 1998, Chapter 11, pp. 417-448.

Holguin, "Consuming a Diet Enriched with Cholinc, UMP, and DHA Improves Memory in Rodents when these Compounds Increase Phospholipids", Massachusetts Institute of Technology, published Mar. 5, 2008.

Holguin, et al. "Chronic administration of DHA and UMP improves the impaired memory of environmentally impoverished rats", Behavioural Brain Research, 2008, vol. 191, pp. 11-16.

Kalmijn, et al. "Polyunsaturated Fatty Acids, Antioxidants, and Cognitive Function in Very Old Men", American Journal of Epidemiology, 1997, vol. 145, No. 1, pp. 33-41.

Luchsinger, et al. "Dietary factors and Alzheimer's disease", The Lancet—Neurology, Oct. 2004, vol. 3, pp. 579-587.

Sakamoto, et al. "Oral supplementation with docosahexaenoic acid and uridine-5'-monophosphate increases dendritic spine density in adult gerbil hippocampus", Brain Research, 2007, vol. 1182, pp. 50-59.

Scheff, et al. "Hippocampal synaptic loss in early Alzheimer's disease and mild cognitive impairment", Neurobiology of Aging, 2006, vol. 27, pp. 1372-1384.

Shah, et al. "The S-Connect study: results from a randomized, controlled trial of Souvenaid in mild-to-moderate Alzheimer's disease", Alzheimer's Research & Therapy, 2013, vol. 5, pp. 1-9.

Welsh, et al. "Detection of abnormal memory decline in mild cases of Alzheimer's disease using CERAD neuropsychological measures", Arch Neurol, Mar. 1991, vol. 48, No. 3, pp. 278-281.

Worley, "Odyssey: Why Do Our Brains Betray Us?—The Fight against Alzheimer's Intensifies". University of Kentucky, Spring 2004, pp. 1-17.

Wurtman, et al. "Synaptic proteins and phospholipids are increased in gerbil brain by administering uridine plus docosahexaenoic acid orally", Brain Research, 2006, vol. 1088, pp. 83-92.

Wurtman, et al., Annals of the New York Academy of Sciences—The Neurobiology of Alzheimer's Disease, 1996, vol. 777.

PALATABLE NUTRITIONAL COMPOSITION COMPRISING A NUCLEOTIDE AND/OR A NUCLEOSIDE AND A TASTE MASKING AGENT

CROSS-REFERENCE TO RELATED APPLICATIONS

This application is a Continuation of patent application Ser. No. 12/809,431, filed as the National Phase of International Patent Application No. PCT/NL2008/050843, filed Dec. 22, 2008, published as WO 2009/082227, which claims priority to PCT/NL2008/050124, filed Mar. 4, 2008 and European Application No. 07123811.7, filed Dec. 20, 2007. The contents of these applications are herein incorporated by reference in their entirety.

FIELD OF THE INVENTION

The present invention relates to the use of a taste masking agent for improving one or more of mouth feel, taste, aftertaste and smell of a liquid aqueous nutritional composition comprising a nucleoside and/or a nucleotide. It also relates to a liquid aqueous nutritional composition comprising a nucleoside and/or nucleotide component, having improved sensory characteristics such as improved mouth feel, taste, aftertaste and smell. In particular, it relates to a composition comprising a nucleoside and/or nucleotide component, in particular comprising an uridine-containing nucleoside and/or a nucleotide in combination with an unsavoury edible oil, such as a fish oil.

BACKGROUND OF THE INVENTION

Memory loss, dementia and reduced brain function are major problems, particularly in elderly. Significant effort is put in the treatment and/or prevention of these disorders related with impaired nerve functioning. Persons older than 50 years of age are particularly prone to developing such disorders.

One way to tackle the problem is the administration of an uridine-containing nucleoside and/or nucleotide, preferably in the form of a nutritional composition.

WO2006/031683 (MIT, 23 Mar. 2006) teaches to administer a composition comprising uridine or a source of uridine, thereby inhibiting or preventing a decline in a cognitive function in a subject, wherein said decline is a result of a cardiovascular disease, neurodegenerative disease, or psychiatric disease. Uridine, in particular in the form of uridine monophosphate (UMP), is a nutrient that increases synthesis and release of neurotransmitters and membrane synthesis by neural cells and brain cells. Nutritional products containing uridine and high concentrations of macro- and micronutrients are administered to elderly patients, with the aim to prevent memory decline.

However, when targeting this group of patients often troubled by reduced appetite or disturbed eating behaviour, such a nutritional product needs to satisfy a number of requirements. It should be readily consumable, thus avoiding an insufficient intake of the active ingredients. For that purpose, it is strived for a product that is desirably palatable and which has a sufficiently low viscosity so it can be easily swallowed.

It is desirable to administer active ingredients to elderly and Alzheimer patients in liquid form. Furthermore, it is highly desirable to administer the active ingredients in a relatively small dosage form such that the administration does not interfere with normal nutritional intake. Additionally palatability is of utmost importance to ensure compliance products need to be consumed for many day, weeks, months or years.

Hence, based on the knowledge that nucleosides/nucleotides, particularly uridine- and/or cytidine-containing nucleotides, are advantageously used by patients suffering from memory impairment, the present inventors designed a liquid composition containing uridine monophosphate suitable for administration to elderly and Alzheimer patients, i.e. a liquid composition prepared by admixing different ingredients including a large amount of uridine monophosphate, edible oils, proteins and preferably also minerals.

However, unexpectedly, the uridine- and/or cytidine-containing nucleotides, in particular the nutritional composition comprising said uridine- and/or cytidine-containing nucleotides had a unpleasant taste, as further characterised by Qualitative Descriptive Analysis (QDA). Uridine as such is rated as "very bitter", uridine monophosphate is rated as "sickly" or "salty". It is the first time that this problem is recognized in the art for this type of product, high in nucleotides and/or nucleosides.

The problem is further aggravated by the fact that the product in question preferably contains a fish oil, having a fishy taste and smell of its own, which is—in combination with the taste of the uridine- and/or cytidine-containing nucleotides experienced as off—tastes like "oily" and "sickly".

Unexpectedly, it was found that mouth feel, taste, aftertaste and smell of a liquid aqueous nutritional composition comprising a nucleoside and/or a nucleotide, and optionally an unsavoury edible oil, in particular a fish oil, could be improved considerably with the use of a taste masking agent selected from the group of starch; cellulose; xanthan gum; gellan gum; alginate; galactomannans such as fenugreek, guar gum, tara gum, locust bean gum, and cassia gum; gum karaya; gum tragacanth; carrageenan; and mixture thereof.

SUMMARY DESCRIPTION OF THE INVENTION

In one aspect, the present invention is concerned with the use of a taste masking agent selected from the group of starch; cellulose; xanthan gum; gellan gum; alginate; galactomannans such as fenugreek, guar gum, tara gum, locust bean gum, and cassia gum; gum karaya; gum tragacanth; carrageenan; and mixture thereof, for improving one or more of mouth feel, taste, aftertaste and smell of a liquid aqueous nutritional composition comprising a nucleoside and/or a nucleotide. Most preferably, the taste masking agent is cellulose.

According to the invention, an improved mouth feel, taste, aftertaste and smell can be qualitatively determined using a QDA panel test which defines and rates mouth feel, taste, aftertaste and smell in a formulation.

It can also be determined in a consumer panel score, and can be expressed as a higher score for overall liking as defined and explained in the experimental section.

In a further aspect, the present invention is concerned with the aforementioned use, wherein the nucleoside is selected from the group of adenosine, guanosine, uridine, cytidine, thymidine, inosine, derivatives thereof, and mixtures thereof and/or the nucleotide is selected from the group of adenosine monophosphate (AMP), adenosine diphosphate (ADP), adenosine triphosphate (ATP), guanosine monophosphate (GMP), guanosine diphosphate (GDP), guanosine triphosphate (GTP), uridine monophosphate (UMP), uridine diphosphate (UDP), uridine triphosphate (UTP), cytidine monophosphate (CMP), cytidine diphosphate (CDP), and cytidine triphosphate (CTP), and mixtures thereof.

In a further aspect, the present invention is concerned with the aforementioned use, wherein the liquid composition further comprises an unsavoury edible oil, in particular a fish oil. Preferably, the fish oil comprises at least one omega-3 fatty acid selected from the group of docosahexaenoic acid (DHA) and eicosapentaenoic acid (EPA).

DETAILED DESCRIPTION OF THE INVENTION

Taste Masking Agent

The present composition according to the invention contains a taste masking agent. Preferably, the present composition contains a taste masking agent selected from the group consisting of starch; cellulose; xanthan gum; gellan gum; alginate; galactomannans such as fenugreek, guar gum, tara gum, locust bean gum, and cassia gum; gum karaya; gum tragacanth; carrageenan; and mixture thereof.

More preferably, the present composition comprises a taste masking agent selected from the group consisting of xanthan gum, gellan gum and cellulose, and mixture thereof. Said taste masking agent preferably have shear-thinning and/or thixotropic properties which are considered beneficial to the formulation or product they are used in. It is even more preferred that the taste masking agent is selected from the group consisting of xanthan gum and cellulose. Most preferably, the present composition comprises cellulose.

According to a special embodiment, the taste masking agent comprises a combination of starch and at least one compound selected from the group of cellulose, cellulose derivatives, xanthan gum, gellan gum, alginate, guar gum, locust bean gum, gum karaya, gum tragacanth, carrageenan, alginic acid and thereof. Said combination has been disclosed in WO 2001/32034 (Smithkline Beecham, 10 May 2001) for masking the taste of an unpalatable edible marine oil. The use of said combination for improving one or more of mouth feel, taste, aftertaste and smell of a liquid aqueous nutritional composition comprising a nucleoside and/or a nucleotide, has not been suggested nor disclosed therein.

According to a preferred embodiment, the present composition contains at least 70 weight % of cellulose based on total weight of taste masking agent.

Preferably, the present composition contains between 0.05 and 3 weight % of one or more of the aforementioned taste masking agents according to the invention, based on total weight of the composition, preferably between 0.1 and 2 weight %, more preferably between 0.3 and 1 weight %.

One of the preferred taste masking agents is starch. Starch is obtainable from a variety of sources, such as, for instance, corn/maize, high amylase maize, waxy maize, potato, rice and wheat, and the starch may be in a pregeletinized or non-pregeletinized form.

Generally preferred are those taste masking agents which are pseudoplastic, such as xanthan, gellan and cellulose.

One of the preferred taste masking agents is the polysaccharide xanthan gum. Its backbone consists of two β-D-glucose units linked through the 1 and 4 positions. The side chain consists of two mannose and one glucuronic acid, so the chain consists of repeating modules of five sugar units. The side chain is linked to every other glucose of the backbone at the 3 position. About half of the terminal mannose units have a pyruvic acid group linked as a ketal to its 4 and 6 positions. The other mannose unit has an acetyl group at the 6 positions. It is preferred to use xanthan gum having pseudoplastic behaviour, and which is stable over a wide range of temperatures and pH.

Gellan gum is a linear tetrasaccharide 4)-L-rhamnopyranosyl-(α-1→3)-D-glucopyranosyl-(β-1→4)-D-glucuronopyranosyl-(β-1→4)-D-glucopyranosyl-(β-1→ with O(2) L-glyceryl and O(6) acetyl substituents on the 3-linked glucose. It is a bacterial exopolysaccharide that is prepared commercially in a manner similar to xanthan gum.

In a preferred embodiment, the composition comprises cellulose. Preferably, the present composition contains between 0.05 and 3 weight % of cellulose, based on total weight of the composition, preferably between 0.1 and 2 weight %, more preferably between 0.3 and 1 weight %. Cellulose is a linear homopolymer of anhydroglucose units linked together by beta-D-1,4 glycosidic bonds. It is preferred to select cellulose from the group consisting of high viscous cellulose and cellulose derivatives such as, for example, hydroxyethyl cellulose, hydroxypropyl methylcellulose (HPMC), carboxymethyl cellulose (CMC), microcrystalline cellulose (MCC) and methyl cellulose.

It was found that excellent results, also in terms of stability, were obtained using large amounts of the non-ionic cellulose ether microcrystalline cellulose.

I was further found that mouth feel, taste, aftertaste and smell of a liquid aqueous nutritional composition according to the invention improved over time, giving an excellent shelf life in yerms of the aforementioned taste attributes.

The taste masking agent of the invention may also act as a thickener for the liquid aqueous nutritional composition according to the invention. Said function has been disclosed in our copending application PCT/NL2008/050124 which is included herein by reference in its entirety.

In this context, it is important to differentiate between slowing precipitation of already formed particles and/or viscosity increase on the one hand, from a decrease in rate and/or prevention of the formation of particles on the other hand. In the present case, it is less important to stabilize already suspended particles. After all, in such case the formation of precipitates would still occur, since with time particles having a higher mass will reach the bottom of the package. In order to solve the problem of the invention, in a main aspect the thickener prevents and/or reduces the formation of the particles, and thus decreases the formation of a sediment on the bottom of a package.

Although the inventors do not wish to be bound by theory, it is hypothesised that the lack of formation of said particles could partly attribute to an improved mouth feel, taste, aftertaste and smell of the liquid aqueous nutritional composition according to the invention.

Due to the limited water-solubility and/or dispersability of the non-ionic cellulose ether, it is preferred that the liquid aqueous nutritional composition according to the invention further contains a respectable amount of an anionic polymeric polysaccharide. In a preferred embodiment, the anionic polysaccharide is selected from the group consisting of guar gum, carboxymethylcellulose, hemicellulose, pectin, alginate, konjac flour, psyllium, gums from tragacanth, xanthan, karaya, chia, wellan, ghatti or okra, or the hydrolysates of these oligo- or polycarbohydrates. These anionic polysaccharides facilitate the manufacture of a stable aqueous food product, in particularly a heat-treated or sterilized liquid product which comprises at least a nucleotide, optionally an unsavoury edible oil, such as a marine oil, and one or more proteins and an further edible oil or fat. The anionic polymeric polysaccharide, such as guar gum or an anionic cellulose, enhances the stability of the aqueous system and prevents aggregation/clothing of cellulose. In one embodiment, it is preferred to use an anionic cellulose, preferably carboxymethyl cellulose (CMC).

In a preferred embodiment, the liquid aqueous nutritional composition according to the invention contains a mixture of MCC and an anionic polymeric polysaccharide, preferably CMC. The liquid aqueous nutritional composition according to the invention preferably comprises 0.05 to 3.0 weight % of a mixture of microcrystalline cellulose (MCC) and an anionic polymeric polysaccharide, based on the total weight of the composition, preferably 0.05 to 1 weight %, more preferably 0.3 to 1.0 weight %. The relative weight ratio of non-ionic cellulose to the anionic polymeric polysaccharide is preferably at least 3:1, more preferably between 4:1 and 9:1. In one embodiment, it is preferred that at least 70 weight %, more preferably 75 to 90 weight % of the cellulose present in the liquid aqueous nutritional composition according to the invention is provided by MCC. Often, MCC is marketed being coated with CMC or cellulose gum. In the most preferred embodiment, the remainder is formed from CMC. Suitable candidates are Avicel-plus BV2312 and Vivapur MCG591F, commercially available with FMC biopolymers and Rettenmaier, respectively. Particularly good results are reported for the latter of the two.

It is further found that optimal characteristics were obtained with taste masking agents having a certain particle size. Preferably, the present taste masking agent is a mixture of particles wherein at least 50 weight % of the particles have a particle size between 20 and 200 micrometer. The bigger particle sizes avoid sedimentation to occur over longer time scales.

The inventors have discovered that the amount of cellulose in the liquid aqueous nutritional composition according to the invention is preferably more than 0.05 weight %, more preferably at least 0.1 weight %, more preferably at least 0.3 weight %, most preferably about 0.4 weight %, based on the total weight of the composition. It is believed that at these concentrations a weak three-dimensional network is built which effectively holds the components in the liquid matrix, the result being no sediment can form and a good taste is obtained. In order to control the viscosity and taste of the composition, it is preferred that the composition contains less than 1.0 weight %, more preferably less than 0.8 weight % of the cellulose.

Apart from the cellulose, gellan and/or xanthan thickeners, it is preferred that the liquid aqueous nutritional composition according to the invention is low in other thickening agents, i.e. substances that are known to increase the viscosity of a composition without substantially modifying its other properties, such as taste. It is preferred that the composition comprises less than 0.1 weight %, more preferably less than 0.05 weight % of such other food thickeners, most preferably none at all. In one embodiment, the weight ratio of compounds having a thickening effect other than cellulose and xanthan over the sum of cellulose and xanthan thickeners of the present invention is less than 0.1, preferably less than 0.01, more preferably 0. More preferably, the weight of compounds having a thickening effect other than cellulose over the sum of the weight cellulose thickeners present in the composition is less than 0.1, more preferably less than 0.01, most preferably 0.

The liquid aqueous nutritional composition according to the invention preferably has a low viscosity, preferably a viscosity between 1 and 100 mPa·s measured at a shear rate of 100 sec$^{-1}$ at 20° C. High viscosities are to be avoided, since these often are associated with unacceptable mouthfeel characteristics and difficulty to be ingested by the target group, e.g. elderly and Alzheimer patients. More preferably, the present composition is preferably provided in the form of a drink capable of being ingested through a straw which makes the product even easier to ingest and improves compliance. In a preferred embodiment the present composition has a viscosity of less than 80 mPa·s at a shear rate of 100 sec$^{-1}$ at 20° C., more preferably of 1 to 40 mPa·s at a shear rate of 100 sec$^{-1}$ at 20° C. These viscosity measurements may be performed using plate and cone geometry. 'Cone and Plate' viscometers use a cone of very shallow angle in bare contact with a flat plate. With this system the shear rate beneath the plate is constant to a modest degree of precision and deconvolution of a flow curve; a graph of shear stress (torque) against shear rate (angular velocity) yields the viscosity in a straightforward manner.

It is preferred that the liquid aqueous nutritional composition according to the invention fulfils FSMP guidelines, and hence contains significant amounts of minerals and vitamins. Hence, typically the product has an osmolality of 300 to 800 mOsm/kg.

To prevent increased viscosity due to gelling of protein, when present, the pH of the liquid is preferably kept around neutral, while for a good palatability the pH is preferably slightly acidic. The liquid aqueous nutritional composition according to the invention preferably has a pH in the range of 5 to 7.5, more preferably 6 to 7.

The liquid aqueous nutritional composition according to the invention preferably has a dry matter content in the range of 10 to 40 weight %, more preferably 10 to 30 weight %.

Nucleoside and Nucleotides

The liquid aqueous nutritional composition according to the invention comprises a nucleoside and/or nucleotide, preferably a nucleotide. A nucleotide is typically more effectively absorbed by the body.

Within the context of this invention, a nucleoside is a glycosylamine consisting of a nucleobase bound to a ribose or deoxyribose sugar. Examples of these include cytidine, uridine, adenosine, guanosine, thymidine and inosine, deoxyderivatives thereof, acylated derivatives thereof, and phosphate derivatives thereof. When a nucleoside is phosphorylated (mono-, di- or tri-), a nucleotide is formed, which is the molecular building block of DNA and RNA.

The liquid aqueous nutritional composition according to the invention comprises at least 50 mg of a nucleotide and/or nucleoside per 100 ml of composition, preferably 80 to 3000 mg of a nucleotide and/or nucleoside per 100 ml of composition, more preferably 100 to 2000 mg of a nucleotide and/or nucleoside per 100 ml of composition, most preferably 200 to 1000 mg of a nucleotide and/or nucleoside per 100 ml of composition.

Preferably, the liquid aqueous nutritional composition according to the invention is characterized by comprising predominantly nucleotides over nucleosides. Hence, the weight ratio of nucleotides over nucleosides is preferably more than 2.0, more preferably more than 4.0, most preferably more than 10.0, in particular more than 20. These ratios are specifically preferred for a liquid aqueous nutritional composition according to the invention with a pH between 2.0 and 8.0, more preferably between 5 and 7.5, more preferably 5.5 and 7.5, most preferably 6 and 7.

The present inventors have found that the invention works particularly well when the liquid aqueous nutritional composition according to the invention comprises uridine or a uridine nucleotide, preferably a uridine nucleotide, preferably at least a uridine nucleotide selected from the group consisting of uridine monophosphate (UMP), uridine diphosphate (UDP), and uridine triphosphate (UTP), or mixtures thereof.

Also, the liquid aqueous nutritional composition according to the invention may comprises cytidine or a cytidine nucleoside, preferably a cytidine nucleotide, preferably at least a cytidine phosphate selected from the group consisting of cytidine monophosphate (CMP), cytidine diphosphate (CDP), and cytidine triphosphate (CTP), or mixtures thereof.

Most preferably, the liquid aqueous nutritional composition according to the invention comprises UMP, as UMP is most efficiently being taken up by the body. Additionally, it was surprisingly found by the inventors that UMP contributes to the product stability, since it binds calcium and thus reduces calcium-induced protein aggregation even further.

Hence, inclusion of UMP in the liquid aqueous nutritional composition according to the invention enables a high efficacy at the lowest dosage and/or the administration of a low volume to the subject. Preferably, at least 50 weight % of the uridine in the liquid aqueous nutritional composition according to the invention is provided by UMP, more preferably at least 75 weight %, most preferably at least 95 weight %. The liquid aqueous nutritional composition according to the invention preferably comprises 0.08 to 3 g uridine per 100 ml of composition, preferably 0.1 to 2 g uridine per 100 ml of composition, more preferably 0.2 to 1 g uridine per 100 ml of composition.

The liquid aqueous nutritional composition according to the invention preferably comprises 0.08 to 3 g UMP per 100 ml of composition, preferably 0.1 to 2 g UMP per 100 ml of composition, more preferably 0.2 to 1 g per 100 ml of composition.

Preferably, the weight ratio of uridine to cytidine is larger than 1.0, more preferably at least 2.0, most preferably more than 5.0. Although cytidine is a precursor of uridine, which passes the blood brain barrier, it is more efficient and effective to include uridine in the present composition.

In a further preferred embodiment, the liquid aqueous nutritional composition according to the invention preferably does not contain high amounts of other nucleotides. Hence, preferably the weight ratio of adenosine to uridine in the present composition is below 0.1, more preferably below 0.01, most preferably 0. Preferably the weight ratio of guanosine to uridine in the present composition is below 0.1, more preferably below 0.01, most preferably 0. Preferably the weight ratio of inosine to uridine in the present composition is below 0.1, more preferably below 0.01, most preferably 0.

Unsavoury Edible Oil

The liquid aqueous nutritional composition according to the invention preferably contains an unsavoury edible oil that is suitably of animal, vegetable or mineral origin. Animal oils are generally derived from the organs and tissues of animals; vegetable oils are commonly derived from plant seeds. Illustrative non-limiting examples of oils include animal oils such as a marine oil such as seal oil, whale oil, krill oil, fish oil such as capelin oil, fish liver oil, e.g. cod liver oil, and fish oils produced from additional body parts (also referred to as fish oils); and vegetable oils such as algae oil, castor oil, soybeen oil, corn oil and linseed oil.

Preferably, the unsavoury edible oil is a fish oil comprising docosahexaenoic acid (22:6 ω-3; DHA), and/or eicosapentaenoic acid (20:5 ω-3; EPA). Therefore, the liquid aqueous nutritional composition according to the invention comprises at least one omega-3 fatty acid selected from the group of docosahexaenoic acid (DHA) and eicosapentaenoic acid (EPA). The liquid aqueous nutritional composition according to the invention preferably comprises 100 to 5000 mg per 100 ml of the sum of one or more of docosahexaenoic acid (DHA) and eicosapentaenoic acid (EPA), more preferably 500 to 3000 mg per 100 ml of composition. This means that preferably at least one of docosahexaenoic acid (DHA) and eicosapentaenoic acid (EPA) is present in the composition according to the invention, whereby the concentration of DHA alone, EPA alone or the sum of EPA and DHA preferably is 100 to 5000 mg per 100 ml, more preferably 500 to 3000 mg per 100 ml of composition.

The present composition preferably contains a very low amount of arachidonic acid (AA; 20:4 ω-6). Preferably the weight ratio DHA/AA in the present composition is at least 5, preferably at least 10, more preferably at least 15. The ratio omega-6/omega-3 fatty acids in the present product is preferably below 0.5, more preferably below 0.2.

Protein

The liquid aqueous nutritional composition according to the invention comprises protein, preferably intact protein. Proteins enable the manufacturing of palatable products. Especially elderly and AD patients benefit from the protein as it strengthens their motor skills. Preferably, the liquid aqueous nutritional composition according to the invention comprises milk protein. Preferably, the liquid aqueous nutritional composition according to the invention comprises a protein selected from the group consisting of whey protein, casein or caseinate. Preferably, the liquid aqueous nutritional composition according to the invention comprises caseinate, more preferably the liquid aqueous nutritional composition according to the invention comprises at least 70 weight %, more preferably at least 90 weight % casein and/or caseinate, based on total protein.

Preferably, the proteins are included in intact (unhydrolyzed) form, in order to have a palatable product. Such high molecular weight proteins increase the viscosity of the heat-treated liquid product, compared to the hydrolyzed forms. The present inventors were able to make an acceptable product, with good palatability and limited viscosity, by applying the measures according the invention, still avoiding precipitation.

Preferably, the liquid aqueous nutritional composition according to the invention comprises between 0.2 and 10 gram protein per 100 ml, preferably between 1 and 6 grams protein per 100 ml, more preferably between 2 and 5 grams protein per 100 ml.

Other Components

Preferably, the liquid aqueous nutritional composition according to the invention further comprises one or more other components, preferably one or more of a mineral, a phospholipid, a digestible carbohydrate, an organic acid, an edible fat other than the unsavoury edible oil, an indigestible carbohydrate, a preservative, a colorant, and a flavouring agent.

Minerals

To fulfil important nutritional requirements, the liquid aqueous nutritional composition according to the invention comprises divalent cations, particularly calcium. Preferably, the liquid aqueous nutritional composition according to the invention comprises 10 to 150 mg calcium per 100 kcal, preferably 40 to 100 mg calcium per 100 kcal. Alternatively or additionally, it is preferred for the liquid aqueous nutritional composition according to the invention to contain 10 to 150 mg calcium per 100 ml, more preferably 40 to 100 mg calcium per 100 ml. The calcium causes particular problems in the aggregation of proteins. Hence, the liquid aqueous nutritional composition according to the invention preferably comprises an insoluble calcium source. In a preferred embodiment, the calcium salt (s) used in the liquid aqueous nutritional composition according to the invention have a solubility below 0.15 gram per 100 ml, more preferably below 0.1 gram per 100 ml, even more preferably below 0.06 gram per 100 ml (demineralised) water at 20° C. and pH 7.

The calcium salt is preferably selected from the group consisting of calcium carbonate, calcium sulphate, calcium citrate (e.g. mono-calcium citrate or tri-calcium citrate), a calcium salt coated with a substance which has limited solubility in water at pH 7 and is soluble at a pH below about 5 (hereafter referred to as coated calcium salts) and mixtures thereof. Examples of coatings and methods for the preparations of coated calcium salts are given in WO0/038829, the entire content of which is hereby incorporated by reference. Preferably the liquid aqueous nutritional composition according to the invention comprises calcium citrate.

In certain embodiments, particularly for compositions containing low amounts of nucleotides or nucleosides, it is be desirable to add phosphate salts. The phosphate salt can be added to provide the mineral requirements to a patient. Preferably, the liquid aqueous nutritional composition according to the invention contains phosphate salts of sodium, potassium, calcium and/or magnesium. The liquid aqueous nutritional composition according to the invention preferably comprises 30 to 80 mg phosphorus per 100 kcal.

Phospholipids

Preferably, the liquid aqueous nutritional composition according to the invention comprises a phospholipid, preferably 0.1 to 50 weight % phospholipids, based on total weight of lipids, more preferably 0.5 to 20 weight %, more preferably between 1 and 5 weight %, based on total weight of lipids. Preferably, the liquid aqueous nutritional composition according to the invention contains at least one selected from the group consisting of phosphatidylcholine, phosphatidylethanolamine, phosphatidylserine and phosphatidylinositol. The total amount of lipids is preferably between 10 and 30 weight % on dry matter, and/or between 2 and 6 g lipid per 100 ml for a liquid composition. Inclusion of phospholipids improve the stability of the liquid aqueous nutritional composition according to the invention.

Digestible Carbohydrates

Advantageously, the liquid aqueous nutritional composition according to the invention comprises digestible carbohydrates. The digestible carbohydrates positively influence the operational skills of a subject, and add to the advantageous effect of the liquid aqueous nutritional composition according to the invention. The liquid aqueous nutritional composition according to the invention preferably contains between 1 and 50 gram digestible carbohydrates per 100 ml of a liquid product, more preferably between 5 and 30 grams per 100 ml, more preferably 10 to 30 grams of carbohydrates per 100 ml. The total amount of digestible carbohydrates is preferably between 25 and 80 weight % on dry matter basis, preferably 40 to 80 weight %.

Organic Acid

Preferably, the liquid aqueous nutritional composition according to the invention comprises an organic acid, preferably 0.5 to 10 weight % organic acid(s) based on total weight of digestible carbohydrates, more preferably 1.5 to 6 weight %. Preferably, the liquid aqueous nutritional composition according to the invention contains citric acid, preferably 0.5 to 10 weight % citric acid based on total weight of digestible carbohydrates, more preferably 1.5 to 6 weight %.

Other Edible Fat

With regard to the type of fat, other than the aforementioned unsavoury edible fat, a wide choice is possible, as long as the fat is of food quality. The fat may include medium chain triglycerides (MCT, mainly 8 to 10 carbon atoms long), long chain triglycerides (LCT) or any combination of the two types. MCTs are beneficial because they are easily absorbed and metabolized. Moreover, the use of MCTs will reduce the risk of nutrient malabsorption. LCT sources, such as rapeseed oil, more in particular rapeseed oil low in erucic acid, sunflower oil, corn oil, palm kernel fat, coconut fat, palm oil, or mixtures thereof are preferred because they provide more energy per unit of fat. In one embodiment, the fat is a liquid fat, i.e. an oil.

Indigestible Carbohydrate

The liquid enteral nutritional composition according to the invention may optionally be fortified with non-digestible carbohydrates (dietary fibres) such as oligosaccharides. These oligosaccharides may comprise fructo-oligosaccharides (FOS), galacto-oligosaccharides (GOS), trans-galacto-oligosaccharides (TOS), xylo-oligosaccharides (XOS), soy oligosaccharides, and the like. Optionally, also higher molecular weight compounds such as inulin, resistant starch and the like may be incorporated in the composition according to the invention. In another embodiment of the present invention, the composition according to the invention may comprise a mixture of neutral and acid oligosaccharides as disclosed in WO 2005/039597 (N.V. Nutricia), which is incorporated herein by reference in its entirety.

Flavouring Agent

The nutritional composition according to the invention may also contain a flavouring agent, either natural, artificial or a mixture thereof. The incorporation of a flavouring agent increases the palatability of the nutritional composition according to the invention, so facilitating its ingestion and imparting a pleasant taste to the nutritional composition. Although the nutritional composition according to the invention without a flavouring agent already tastes pleasant, adding a flavouring agent to impart a particular flavour may further improve the palatability, thus increasing patient compliance. Often used flavours are chocolate, vanilla, coffee, caramel, cinnamon, strawberry, lemon, peach, orange, forest fruits, creamy flavour, nutty, coconut, etc. The nutritional composition according to the invention may also contain an artificial sweetener, such as, for instance saccharin, aspartame and the like. Other embodiments will be clear to those skilled in the art. A particular preferred flavouring agent is selected from the group of vanilla, creamy flavour, nutty, coconut and caramel. Suitable flavourings may be used, individually or as a mixture, in an amount ranging from about 0.005 weight % to about 2.0 weight % of the composition, preferably in an amount of less than 1 weight %. Amounts can be easily determined by the skilled person and depend on the application, taste requirements, etc.

Further Features

Persons suffering from neuropathies or neurological problems often experience problems with eating. Their sensory capabilities and/or control of muscles has become imparted, as well as in some instances their ambition to apply proper eating habits. Part of these patients may experience a general loss in appetite and a relatively large part of this patient group became malnourished. Preferably the product has an energy density of 0.8 to 4.5 kcal per gram of the composition, more preferably between 0.9 and 2.5 kcal per ml.

Liquid nutritional products preferably have a long shelf life. However, increasing shelf life by heat treatments often results in destabilisation of the products and/or palatability, leading to a product which is unacceptable. The liquid aqueous nutritional composition according to the invention can be subjected to a heat treatment without major adverse effects on the palatability. Hence, the liquid aqueous nutritional composition according to the invention is preferably heat-treated, more preferably the composition is subjected to a sterilization process. In a preferred embodiment, the liquid aqueous nutritional composition according to the invention is subjected to an ultra-high temperature treatment (UHT-process). Such UHT-process is preferably applied in line, i.e. before the liquid final product is filled in the package of the sold unit.

Application

Although the invention in a particular embodiment pertains in particular to the use of the liquid composition according to the invention for preventing and/or treating neurodegenerative disorders, preferably selected from the group consisting of memory decline and/or cognitive dysfunction, Alzheimer's, Parkinson's and/or dementia, and in particular to the use of the composition according to the invention for promoting or supporting healthy brain function, it also pertains in general to any composition comprising a unsavoury nucleoside and/or nucleotide component, in particular comprising an uridine-containing nucleoside and/or a nucleotide in combination with an unsavoury edible oil, such as a fish oil, for any particular use.

The composition is particularly useful for the dietary management of subjects suffering from neurodegenerative disorders, preferably selected from the group consisting of memory decline and/or cognitive dysfunction, Alzheimer's, Parkinson's and/or dementia.

The present composition is preferably administered in doses of between 25 and 500 ml of the present composition, preferably between 50 and 250 ml, preferably between 75 and 150 ml. Preferably, the composition is administered once a day. Relatively limited volumes are easy to ingest by the target patients groups, e.g. elderly and AD patients, preferably a person older than 50 years of age.

EXPERIMENTAL

Study Design

Figure 1:
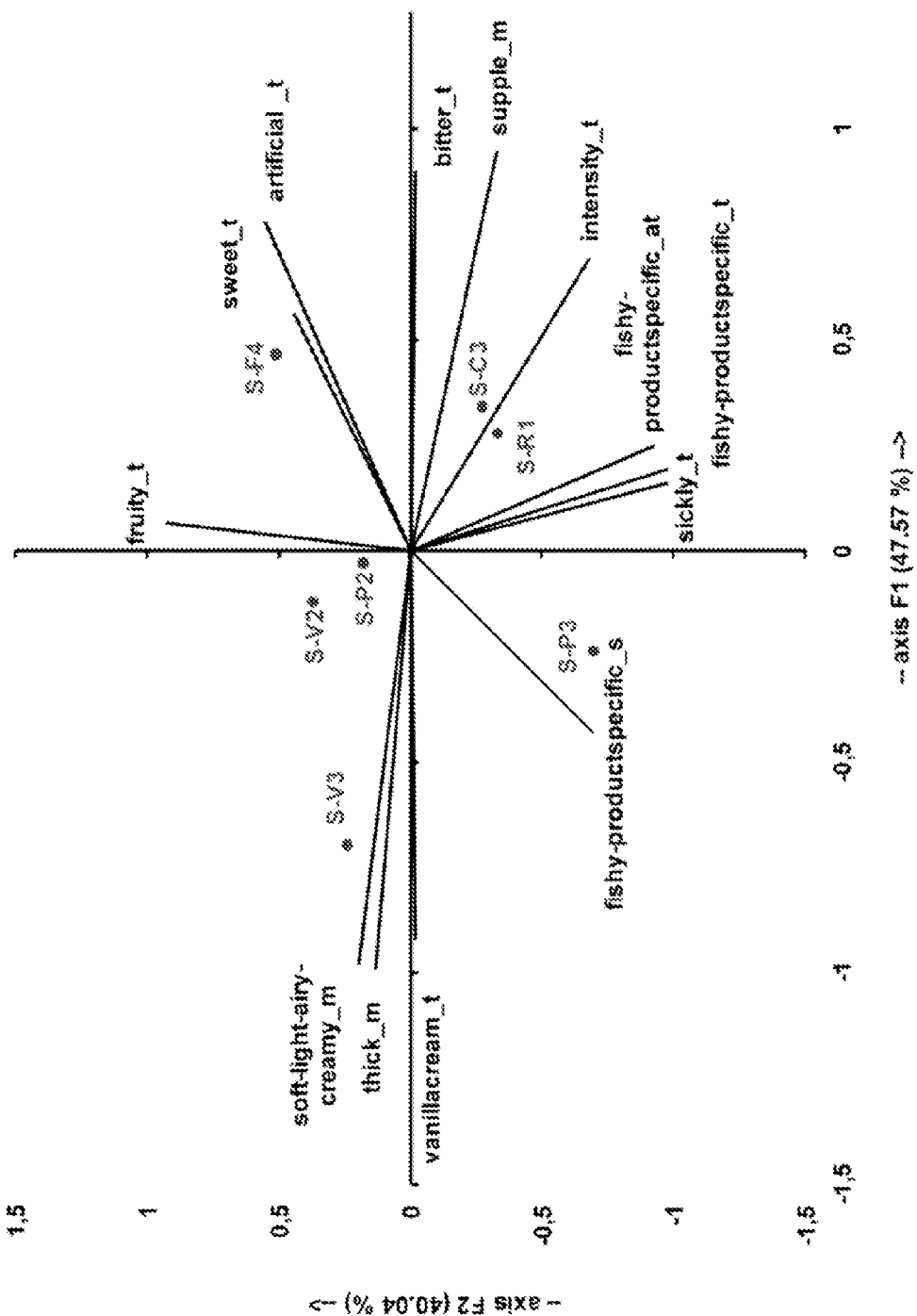
FIG. 1: Biplot after Varimax rotation (axes F1 and F2: 87.61%) for the various formulations (see Table 2). m=mouth feel; s=smell; t=taste; at=aftertaste.

Qualitative Descriptive Analysis (QDA) was performed on a series of formulations that varied in amount of protein, fat, taste masking agent, and maltodextrin/sucrose ratio (Table 1 for the reference formula and FIG. 1). All batches of the formulation were prepared with orange/peach flavours. The study was conducted as a single blind sip feed evaluation of the formulations on 19 attributes, using a QDA panel with 11 trained assessors and scoring on 100 mm line scale. This QDA panel generates attributes (such as fishy, intensity, fruity, sickly, etc.), which describe the product, without indicating if the products are most or least appreciated (hedonic scale).

Statistical analyses were done using XLSTAT 7.5.2. Principal Component Analysis (PCA) (Addinsoft SARL) using uniform weighting and a varimax rotation of the axes. Differences are found significant at a significance level of 0.05 (two-tailed test).

The objective of this research was to analyse if the amount of protein, fat, taste masking agent or maltodextrin/sucrose ratio influences the amount of off-notes (mouth feel, taste, after taste and smell) in the formulation.

The following reference formulation was used (Table 1).

TABLE 1

| Ingredients (per 100 ml) | Reference |
|---|---|
| Energy | 100 kcal |
| Protein (casein/whey 80/20) | 3.06 g |
| Carbohydrates | 13.3 g including |
| maltodextrin/sucrose | 7.2 g/6.0 g |
| Fat (fish oil, phospholipids) | 3.73 g including: |
|  | 0.96 g DHA |
|  | 0.24 g EPA |
| Uridine monophosphate (disodium salt) | 0.5 g |
| Taste masking agent | 0 g |
| Choline | 0.32 g |
| Vitamin E | 32 mg |
| Vitamin C (Alpha-tocopherol) | 64 mg |
| Selenium | 48 mcg |
| Vitamin B6 | 0.8 mg |
| Folic acid | 0.32 mg |
| Vitamin B12 | 2.4 mcg |
| Magnesium | 20 mg |
| Zinc | 1.2 mg |
| Manganese | 0.3 mg |
| Molybdenum | 10 mcg |
| Na | 0.1 g |
| K | 0.15 g |
| Cl | 0.12 g |
| Ca | 80 mg |
| P | 70 mg |
| Fe | 1.6 mg |
| I | 27 mcg |
| Cu | 0.18 mg |
| Cr | 6.7 mcg |
| F | 0.1 mg |
| Vitamin A | 0.16 mg |
| Vitamin B1 | 0.15 mg |
| Vitamin B2 | 0.16 mg |
| Vitamin B3 | 1.8 mg |
| Vitamin B5 | 0.53 mg |
| Vitamin D | 0.7 mcg |
| Biotin | 4.0 mcg |
| Vitamin K | 5.3 mcg |

Experiment 1

The following formulations were tested (Table 2):

TABLE 2

| | |
|---|---|
| S-R1 | Reference (see Table 1) |
| S-F4 | Fish oil replaced by canola oil |
| S-P2 | Protein amount raises up to 6 g/100 ml |
| S-P3 | Protein amount raises up to 6 g/100 ml and added an extra 2.3 g/100 ml of canola oil |
| S-C3 | 7.8 g sucrose and 5.4 g maltodextrin |
| S-V2 | Added 0.4% cellulose as taste masking agent |
| S-V3 | Added 0.8% cellulose as taste masking agent |

The QDA results show that, compared to reference S-R1, the addition of more protein (S-P2, S-P3) or taste masking agent (S-V2, S-V3) gave less product specific taste, after taste and smell and the so named "sickly taste" was also clearly reduced. However, addition of extra canola oil (S-P3) or more sucrose than maltodextrin (S-C3) did not contribute to the reduction of negative attributes.

Figure 2A:
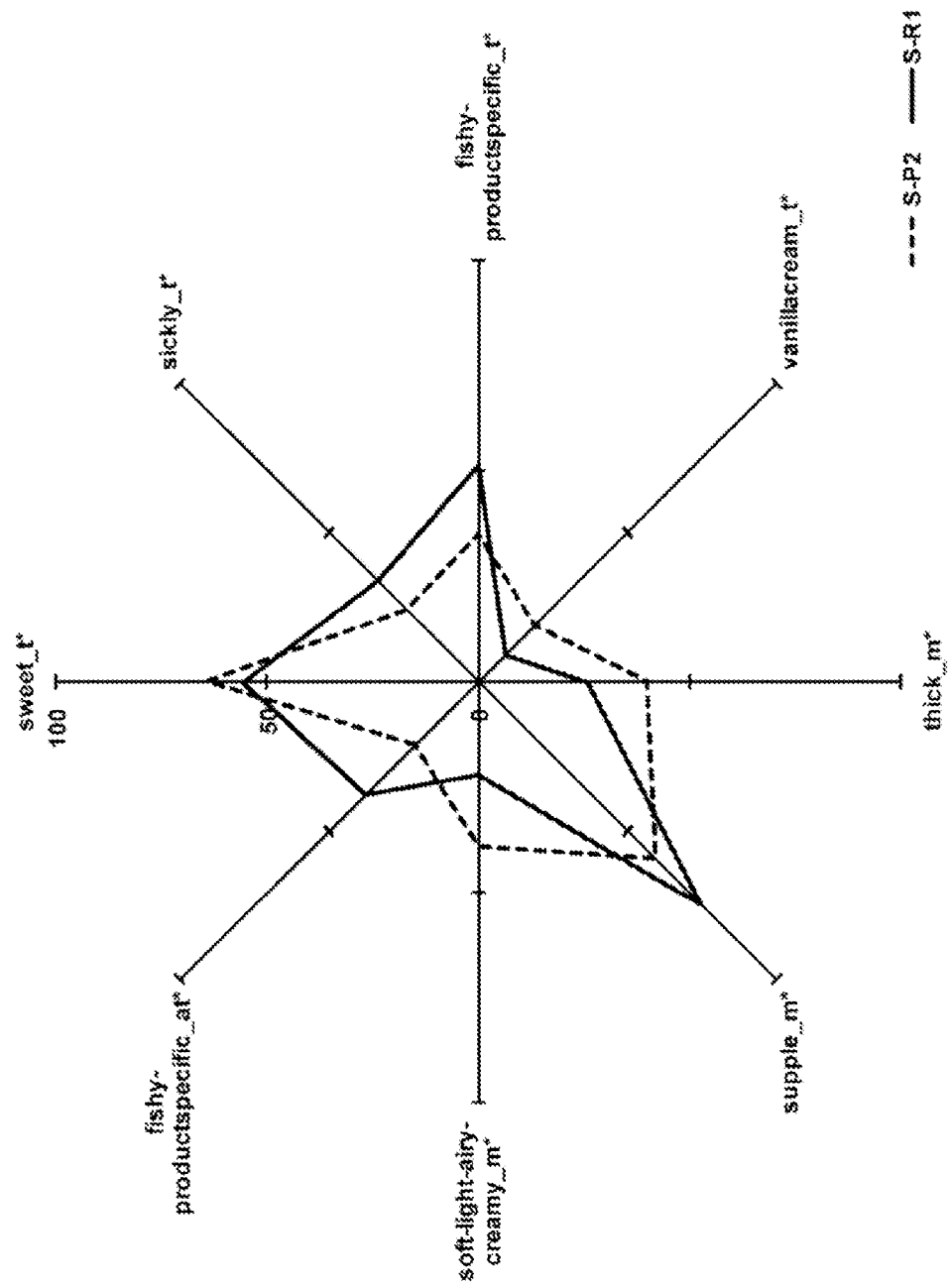
FIG. 2: a) Spider R1 (sold line) versus P2 (dotted line) and b) R1 (sold line) versus V2 (dotted line); the * indicates a significant different attribute. m=mouth feel; s=smell; t=taste; at=aftertaste.
Figure 2B:
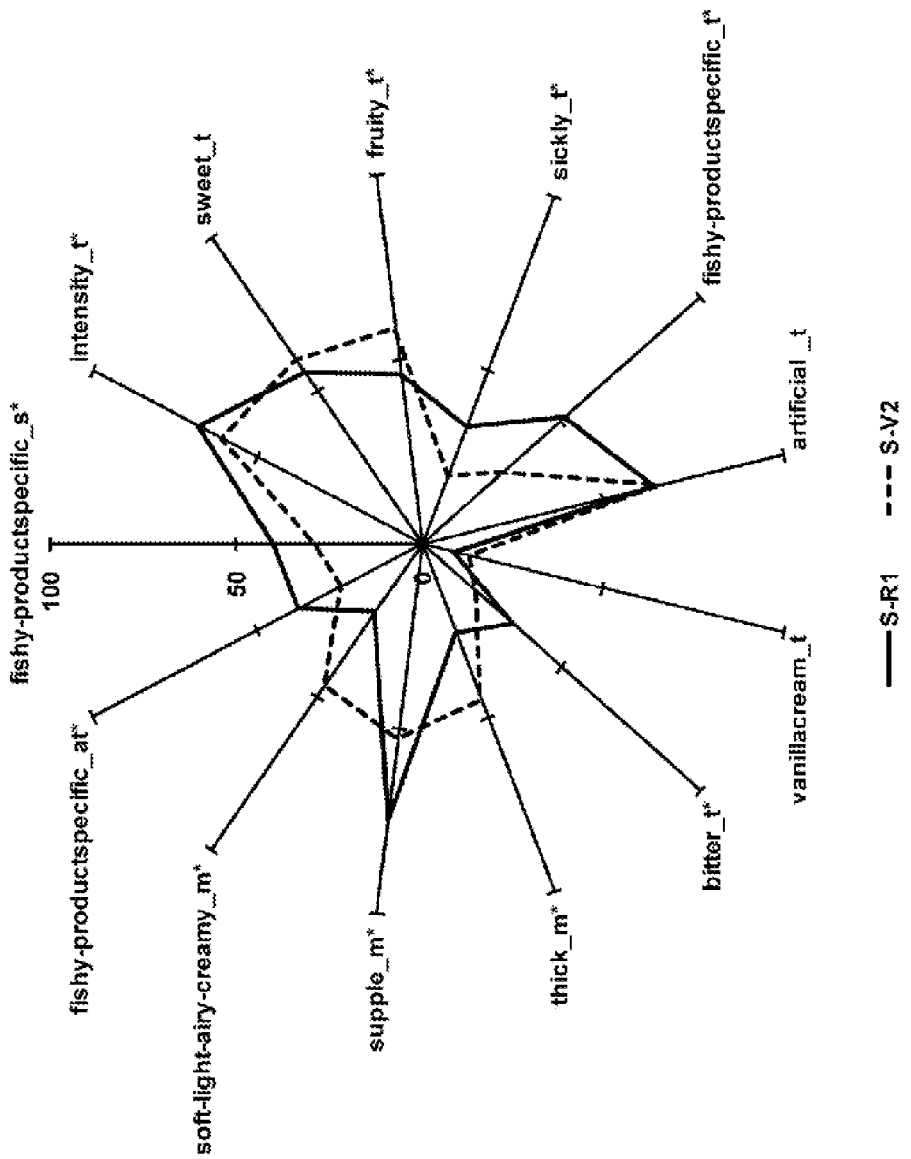

With addition of protein or taste masking agent the product is thicker and gives a creamier mouth feel. This makes the fat globules less accessible to the tongue and nucleotide and fish taste awareness will be reduced. Comparison of the 6 g/100 ml protein batch (S-P2) and 0.4% taste masking agent batch (S-V2) with the reference batch (S-R1) is also shown in FIG. 2a and FIG. 2b. No further significant improvements could be obtained with addition of higher taste masking agent concentrations (S-V3). Furthermore, a part of the fishy off-notes are (volatile) aldehydes which can bind to e.g. lysine or glutamine. During shelf life this binding will increase and the amount of off-notes will decrease, leading to the finding that the palatability increased with increasing shelf life.

In case of addition of more canola oil (S-P3), it was expected that the fish oil would be diluted and consequently the fish taste would be reduced. However, with increase of the oil content, it appears that more oil is available to be in contact with the tongue surface and as a result, the fish taste is perceived stronger.

Increased sweetness had a lower impact on the masking off-notes than addition of more protein or taste masking agent.

Experiment 2

Figure 3:
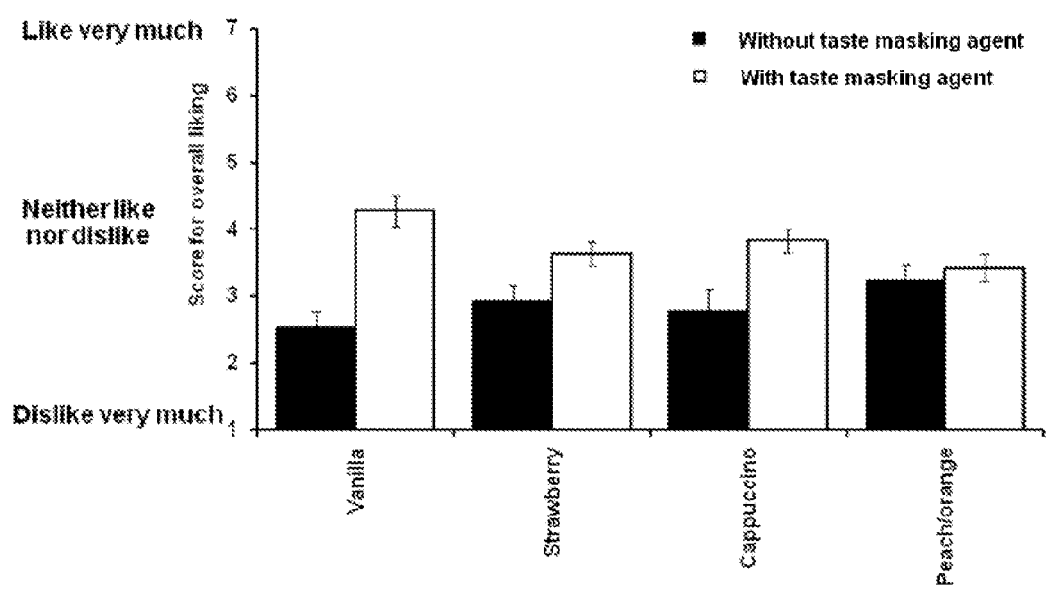
FIG. 3: Consumer panel results of four flavor concepts (vanilla, strawberry, cappuccino and peach/orange).

Four flavour concepts (vanilla, strawberry, cappuccino and peach/orange) of the reference formulation (S-R1) and of the formulation with 0.4% of cellulose taste masking agent (S-V2) were analysed in an internal consumer panel. This panel scored products from "dislike very much" to like very much. Results are summarized in FIG. 3. All flavour variants contained the same flavours (and concentrations) in all flavour developments, which indicates that addition of 0.4% of cellulose has increased the scores, wherein vanilla has the highest score.

CONCLUSION

Addition of extra protein or taste masking agent reduces fish product specific taste, smell and after taste as well as the "sickly" taste of the formulation according to the invention. Flavour development has shown that addition of 0.4% cellulose increased scores significantly for different flavours.

The invention claimed is:

1. A liquid composition having a viscosity between 1 and 100 mPa·s measured at a shear rate of 100 sec$^{-1}$ at 20° C., comprising:
   (a) at least 50 mg per 100 ml of composition of uridine, cytidine, and/or a deoxy-, acetylated-, and/or a nucleotide-form thereof, and
   (b) one or more polysaccharides selected from the group consisting of starch; cellulose; xanthan gum; gellan gum; alginate; galactomannans; gum karaya; gum tragacanth; and carrageenan, in an amount effective to improve mouth feel, taste, aftertaste and/or smell of the uridine, cytidine, and/or a deoxy-, acetylated-, and/or a nucleotide-form thereof.

2. The liquid composition according to claim 1, wherein the nucleotide-form is selected from uridine monophosphate (UMP), uridine diphosphate (UDP), uridine triphosphate (UTP), cytidine monophosphate (CMP), cytidine diphosphate (CDP), and cytidine triphosphate (CTP), and mixtures thereof.

3. The liquid composition according to claim 2, comprising UMP in an amount of 0.08 to 3 g per 100 ml of the composition.

4. The liquid composition according to claim 1, wherein the galactomannans are selected from the group consisting of fenugreek, guar gum, tara gum, locust bean gum, and cassia gum.

5. The liquid composition according to claim 1, comprising between 0.05 and 3 weight % of the polysaccharides, based on total weight of the composition.

6. The liquid composition according to claim 1, comprising a cellulose selected from the group consisting of high viscous cellulose, hydroxyethyl cellulose, hydroxypropyl methylcellulose (HPMC), carboxymethyl cellulose (CMC), microcrystalline cellulose (MCC) and methyl cellulose.

7. The liquid composition according to claim 6, comprising 0.5 to 1 weight %, based on the total weight of the composition, of a mixture of MCC and an anionic polymeric polysaccharide.

8. The liquid composition according to claim 7, wherein the anionic polymeric polysaccharide is carboxymethyl cellulose.

9. The liquid composition according to claim 1, further comprising one or more of a protein and a flavouring agent.

10. The liquid composition according to claim 9, comprising between 0.2 and 10 gram protein per 100 ml.

11. The liquid composition according to claim 9, wherein flavouring agent is selected from the group consisting of vanilla, creamy flavour, nutty, coconut and caramel.

12. The liquid composition according to claim 1, further comprising a fish oil.

13. The liquid composition comprising according to claim 1, further comprising between 100 to 5000 mg of the sum of one or more of docosahexaenoic acid and eicosapentaenoic acid per 100 ml.

14. A method for treating a patient suffering from a neurodegenerative disorder, the method comprising administering to the patient the liquid composition according to claim 1.

15. The method according to claim 14, wherein the neurodegenerative disorders is selected from the group consisting of memory decline and/or cognitive dysfunction, Alzheimer's, Parkinson's and/or dementia.

* * * * *